United States Patent [19]

Yokoyama et al.

[11] Patent Number: 5,795,633

[45] Date of Patent: Aug. 18, 1998

[54] MATERIAL COMPOSITION AND SHAPED ARTICLE

[75] Inventors: Tetsuo Yokoyama; Kyoko Hiraoka, both of Nagasaki; Hiroto Kidokoro, Kamakura, all of Japan

[73] Assignee: Nippon Zeon Co., Ltd., Tokyo, Japan

[21] Appl. No.: 793,253

[22] PCT Filed: Aug. 21, 1995

[86] PCT No.: PCT/JP95/01649

§ 371 Date: Feb. 21, 1997

§ 102(e) Date: Feb. 21, 1997

[87] PCT Pub. No.: WO96/05871

PCT Pub. Date: Feb. 29, 1996

[30] Foreign Application Priority Data

Aug. 22, 1994 [JP] Japan .................................. 6-219541
Jul. 5, 1995 [JP] Japan .................................. 7-210156
Jul. 18, 1995 [JP] Japan .................................. 7-203950

[51] Int. Cl.$^6$ .................................................. C08G 18/48
[52] U.S. Cl. .......................... 428/35.7; 428/36.9; 604/96; 606/194; 528/60; 528/76
[58] Field of Search ................... 528/76, 60; 604/96; 606/194; 428/35.7, 36.9

[56] References Cited

U.S. PATENT DOCUMENTS

| | | | |
|---|---|---|---|
| 4,156,066 | 5/1979 | Gould | 528/73 |
| 4,371,686 | 2/1983 | Yamamoto et al. | 528/76 |
| 5,061,254 | 10/1991 | Karakelle et al. | 604/265 |
| 5,468,834 | 11/1995 | Finsterwalder et al. | 528/60 |

FOREIGN PATENT DOCUMENTS

| | | |
|---|---|---|
| 0 417 553 A2 | 3/1991 | European Pat. Off. |
| 62-22818 | 1/1987 | Japan. |
| 62-2949 | 1/1987 | Japan. |

*Primary Examiner*—Rachel Gorr
*Attorney, Agent, or Firm*—Armstrong, Westerman, Hattori, McLeland & Naughton

[57] ABSTRACT

A material composition comprising (a) a poly-functional isocyanate, (b) a compound having MW of 600–3,500 and two functional groups polymerizable with an isocyanate group, (c) a compound having MW below 500 and two functional groups polymerizable with an isocyanate group, and (d) a compound having MW below 700 and at least three functional groups polymerizable with an isocyanate group. A shaped polymeric material is made by mixing and heating (a) with part of (b) to give a prepolymer, adding the remainder of (b), (c) and (d) to the prepolymer, and then heating the mixture to effect additional polymerization of (a), (b), (c) and (d). The shaped polymeric material has enhanced tear strength, tensile strength and elongation, reduced permanent set and low toxicity, and suitable for parts for which high stretchability is required.

20 Claims, No Drawings

MATERIAL COMPOSITION AND SHAPED ARTICLE

DESCRIPTION

1. Technical Field

This invention relates to a shaped article and a material composition. More particularly, it relates to a medical shaped article used as parts for which a high stretchability is required, such as a balloon of a catheter, and having a low toxicity, a high tear strength, a high tensile strength, a large elongation and a reduced permanent set, and to a material composition used for the medical shaped article.

2. Background Art

For medical articles used as treating living bodies such as a catheter and an artificial vessel, a low toxicity, a high tear strength, a high tensile strength, a large elongation and a reduced permanent set are required.

As a material used for a shaped article such as a balloon of a catheter, natural rubber is well known. However, it has recently been found that natural rubber contains a trace amount of protein and causes a biological allergic reaction. Therefore a material composition which can be a substitute for natural rubber is eagerly desired.

As a natural rubber substitute, a thermoplastic polyurethane is known. A thermoplastic polyurethane is a polymer prepared by a polycondensation reaction between approximately equimolar amounts of a diisocyanate and a diol or diamine. However, as is known in the art, in the case where a thermoplastic polyurethane is used for a part such as a catheter balloon, for which a 500% or higher elongation is required, when the balloon contracts, it is creased and a blood stream becomes locally stagnant and a salient amount of thrombus is produced. Further, a shaped article made of a thermoplastic polyurethane has a low tensile strength and elongation, as compared with natural rubber, and a large permanent set. Thus a thermoplastic polyurethane cannot be a perfect substitute for natural rubber.

It is conducted that molecule chains of a thermoplastic polyurethane are crosslinked with a cross-linking agent having at least three functional groups or other crosslinkers to reduced the permanent set of the thermoplastic polyurethane. However, the crosslinked thermoplastic polyurethane has a low tensile strength and tear strength, and therefore is not suitable for shaped articles for which high tenacities are required.

DISCLOSURE OF INVENTION

An object of the present invention is to provide a shaped article suitable as parts for which a high stretchability is required, and having a low toxicity, a high tear strength, a high tensile strength, a large elongation and a reduced permanent set, and to a material composition used for the shaped article.

The inventors have conducted researches to achieve the above objects, and found that, when a polyurethane made by using a specific chain extender is used, the above object can be achieved, and completed the present invention.

In accordance with the present invention, there is provided a material composition characterized as comprising, as the essential ingredients:

(a) a polyfunctional isocyanate, (b) a compound having a molecular weight of 600 to 3,500 and two functional groups capable of being additionally polymerized with an isocyanate group, (c) a compound having a molecular weight not larger than 500 and two functional groups capable of being additionally polymerized with an isocyanate group, and (d) a compound having a molecular weight not larger than 700 and at least three functional groups capable of being additionally polymerized with an isocyanate group;

the sum of the functional groups capable of being additionally polymerized with an isocyanate group, in compounds (c) and (d), is 1 to 35 moles per 100 moles of the isocyanate groups in polyfunctional isocyanate (a), the amount of the functional group capable of being additionally polymerized with an isocyanate group, in compound (d), is 0.1 to 18 moles per 100 moles of the isocyanate groups in polyfunctional isocyanate (a), the amount of the functional group capable of being additionally polymerized with an isocyanate group, in compound (b), is 60 to 100 moles per 100 moles of the isocyanate groups in polyfunctional isocyanate (a), and the sum of the functional groups capable of being additionally polymerized with an isocyanate group, in compounds (b), (c) and (d), is 80 to 110 moles per 100 moles of the isocyanate groups in polyfunctional isocyanate (a).

In accordance with the present invention, there is further provided a shaped article made of a polymer prepared by additional polymerization of polyfunctional isocyanate (a) with compound (b), compound (c) and compound (d).

BEST MODE FOR CARRYING OUT THE INVENTION

The invention will now be described in detail in the following.

The material composition of the present invention comprises, as the essential ingredients, (a), a polyfunctional isocyanate, and compounds (b), (C) and (d) which have a specific molecular weight and functional groups capable of being additionally polymerized with an isocyanate group.

Polyfunctional isocyanate (a) used in the material composition of the present invention is a compound having two isocyanate groups. As specific examples of polyfunctional isocyanate (a), there can be mentioned aromatic diisocyanates such as diphenylmethane diisocyanate, naphthalene diisocyanate, tolylene diisocyanate, tetramethylxylene diisocyanate and xylene diisocyanate; and aliphatic diisocyanates such as dicyclohexane diisocyanate, dicyclohexylmethane diisocyanate, hexamethylene diisocyanate and isophorone diisocyanate. Of these polyfunctional isocyanates, diphenylmethane diisocyanate is most preferable in view of high safety to living bodies.

Compound (b) used in the material composition of the present invention is a compound having two functional groups capable of being additionally polymerized with an isocyanate group. The functional group capable of being additionally polymerized with an isocyanate group is a functional group having active hydrogen. By the term "active hydrogen" used herein is meant a hydrogen atom bonded to an oxygen atom or a nitrogen atom which constitute part of the compound. As specific examples of the functional group, there can be mentioned a hydroxyl group and an amino group.

Compound (b) having two functional groups capable of being additionally polymerized with an isocyanate group (which group is hereinafter abbreviated to "functional group") has a molecular weight of at least 600, preferably at least 700, and not higher than 3,500, preferably not higher than 2,500. If the molecular weight of compound (b) is lower than 600, a shaped article made by additionally polymerizing the material composition has a poor tensile strength and a small elongation. In contrast, if the molecular weight thereof exceeds 3,500, the material composition becomes difficult to shaper and, even if it is possible to shape, the shaped article has an undesirably large permanent set. The molecular weight of compound (b) means that as determined by measurement by gel permeation chromatography using tetrahydrofuran as a carrier and calculation based on a calibration curve of the number average molecular weight of standard polystyrene.

Compound (b) having two functional groups preferably has a weight average molecular weight/number average molecular weight of not larger than 2, preferably not larger than 1.9 If the ratio exceeds 2, the shaped article tends to have a large permanent set and a poor tensile strength. The weight average molecular weight of compound (b) means that as determined by measurement by gel permeation chromatography using tetrahydrofuran as a carrier and calculation based on a calibration curve of the weight average molecular weight of standard polystyrene.

As specific examples of compound (b) having two functional groups, there can be mentioned polyether-diols such as polyoxy-tetramethylene glycol, polyethylene glycol and polypropylene glycol, dehydration condensates of a polycarboxylic acid such as adipic acid with a polyhydric alcohol such as a glycol or a triol, a polyester-diol such as polycarbonate-diol, and polybutadiene diol. Compound (b) may be used either alone or in combination. Among the these compounds (b), a polyetherdiol, especially polyoxytetramethylene glycol is preferable because of biological acceptability and safety.

The amount of compound (b) is such that the amount of the functional group within compound (b) is 60 to 100 moles, preferably 70 to 95 moles, per 100 moles of the isocyanate group (when appropriate, hereinafter referred to merely as "isocyanate group") within polyfunctional isocyanate (a). If the amount of the functional group in compound (b) is smaller than 60 moles, the shaped article has a poor tensile strength and a small elongation. In contrast, if the amount of the functional group in compound (b) is larger than 100 moles, the shaped article has a large permanent set.

Compound (c) used in the material composition of the present invention is a compound having two functional groups.

Compound (c) has a molecular weight of not higher than 500, preferably not higher than 400. The lower limit of the molecular weight is usually about 30. If the molecular weight is larger than 500, the shaped article has a low tenacity. The molecular weight of compound (c) is determined by mass spectrometry.

As specific examples of compound (c), there can be mentioned dials such as ethylene glycol, diethylene glycol, propylene glycol, 1,4-butanediol and 1,6-hexanediol, and diamines such as ethylenediamine, hexamethylenediamine, N,N'-diisopropylmethylenediamine and N,N'-di-sec.-butyl-p-phenylenediamine. Of these compounds (c), ethylenediamine and 1,4-butanediol are preferable because the shaped article has a high tenacity.

Compound (d) used in the material composition of the present invention is a compound having at least three functional groups.

Compound (d) has a molecular weight of not higher than 700, preferably not larger than 600. If the molecular weight thereof is higher than 700, the shaped article has a poor tenacity. The lower limit thereof is usually about 40. The molecular weight of compound (d) is determined by mass spectrometry.

As specific examples of compound (d), there can be mentioned tri- or more functional polyols such as glycerine, trimethylolpropane, pentaerythritol, sorbitol, methylene glycoside, N-tetrapropinol-diethylamine and sucrose, and tri- or more functional polyamines such as 1,3,5-triaminobenzene. Of these compounds (d), trimethylolpropane is preferable.

Among the combinations of compound (c) with compound (d), a combination of ethylenediamine or 1,4-butanediol as compound (c) with trimethylolpropane as compound (d) is preferable in order to provide a shaped article having a high tear strength, a high tensile strength and a small permanent set.

The sum of compound (c) and compound (d) is such that the total amount of the functional groups in compound (c) and compound (d) is 1 to 35 moles, preferably 3 to 35 moles, per 100 moles of the isocyanate group.

The amount of compound (c) is such that the amount of the functional group in compound (c) is 0.9 to 34.9 moles, preferably 2 to 34 moles, per 100 moles of the isocyanate group.

The amount of compound (d) is such that the amount of the functional group in compound (d) is 0.1 to 18 moles, preferably 1 to 10 moles, per 100 moles of the isocyanate group.

The ratio of compound (c) to compound (d) is such that the ratio of the amount of the functional group in compound (c) to the total amount of the functional group in compound (c) plus compound (d) is 70 to 97% by mole, preferably 80 to 95% by mole, and that the ratio of the amount of the functional group in compound (d) to the total amount of the functional group in compound (c) plus compound (d) is 3 to 30% by mole, preferably 5 to 20% by mole. If the relative amount of compound (c) is too small, the shaped article tends to have a poor elongation and a low tear strength. In contrast, if the relative amount of compound (c) is too large, there is a tendency to reduce the effect of enhancing tear strength and tensile strength of the shaped article.

The sum of compound (b), compound (c) and compound (d) is such that the total amount of the functional group in compound (b), compound (c) plus compound (d) is 80 to 110 moles, preferably 85 to 105 moles, and more preferably 90 to 105 moles, per 100 moles of the isocyanate groups The sum of the three compounds is outside this range, the shaped article has a large permanent set.

According to the need, the material composition of the present invention may have incorporated therein additives, which include fillers such as colloidal silica, white carbon and calcium carbonate; plasticizers such as dibutyl phthalate, di(2-ethylhexyl) phthalate and di(2-ethylhexyl) adipate; softeners such as white oil and paraffin, and reaction promotors for the reaction of polyfunctional isocyanate (a) with compound (b), compound (c) and compound (d) such as a tertiary amine and an alkyl-tin.

The configuration of the material composition of the present invention is not particularly limited, A material composition prepared by a process wherein a mixture of polyfunctional isocyanate (a), part of compound (b), part of compound (c) and part of compound (d) is heat-melted, and a mixture of the remainders of compound (b), compound (c) and compound (d) is heat-melted, and then the two molten mixtures are mixed together, can be shaped into a shaped article by casting the molten mixture in a mold. A material composition prepared by dissolving polyfunctional isocyanate (a), compound (b)e compound (c) and compound (d) in an organic solvent can be shaped into a shaped article by a dip forming method. It is preferable that the solution in an organic solvent for dip forming contains compound (b), compound (c) and compound (d) in amounts such that the total amount of functional groups in the sum of compound (b), compound (c) and compound (d) is not larger than 95 moles per 100 moles of the isocyanate groups in the polyfunctional isocyanate (a). If the total amount of functional groups in compound (b), compound (c) and compound (d) exceeds 95 moles, premature additional polymerization of the polyfunctional isocyanate (a) with compound (b), compound (a) and compound (d) occurs and the solute is liable to be deposited, and thus, the dip forming of the, solution becomes difficult.

The organic solvent used for the preparation of the forming solution is usually either incompatible with water or, when it is compatible with water, the aqueous solution of the organic solvent has a pH value of 6 to 8. As specific examples of the organic solvent, there can be mentioned aromatic hydrocarbons such as benzene, toluene and xylene; ethers such as tetrahydrofuran and cyclohexanone; ketones such as methyl ethyl ketone and isobutyl ethyl ketone; aliphatic hydrocarbons such as hexene and hexane; and acetonitrile, dimethylsulfoxide, N,N-dimethylformamide and dimethylacetamide.

The method for preparing the material composition of the present invention is not particularly limited. Various methods can be employed, which include, for example, a method wherein polyfunctional isocyanate (a) is mixed with compound (b), and then compound (c) and compound (d) are added; a method compound (b), compound (c) and compound (d) are mixed together and then polyfunctional isocyanate (a) is added; and a method wherein polyfunctional isocyanate (a) is mixed with part of compound (b), and then the remainder of compound (b), compound (c) and compound (d) are added. Of these methods, the method wherein polyfunctional isocyanate (a) is mixed with part of compound (b), and then the remainder of compound (b), compound (c) and compound (d) are added is preferable because a shaped article having a high tensile strength is obtained.

In the method wherein polyfunctional isocyanate (a) is mixed with part of compound (b) at the first step, and the remainder of compound (b), compound (c) and compound (d) are added at the second step, the amount of compound (b) mixed with polyfunctional isocyanate (a) at the first step is such that the amount of the functional group in the compound (b) is usually 35 to 65 moles, preferably 40 to 60 moles, per 100 moles of the isocyanate group. If the amount of the functional group in the compound (b) is larger than 65 moles or smaller than 35 moles, the effect of enhancing the tensile strength is occasionally reduced.

At the time when or after polyfunctional isocyanate (a) is mixed with part of compound (b), it is preferable to heat the mixture of (a) with (b). By heating the mixture, polyfunctional isocyanate (a) is additionally polymerized with part of compound (b). The heating temperature is usually 50° to 100° C., preferably 60° to 90° C. When the heating temperature is lower than 50° C., a long period of time is required for completion of the additional polymerization. When the heating temperature is higher than 100° C., the procedure at the second step becomes difficult to conduct, as well as the shaped article has a large permanent set, and poor tensile strength, tear strength and elongation. The heating time is usually 10 to 480 minutes, preferably 30 to 120 minutes.

After the completion at the first step, the remainder of compound (b), compound (c) and compound (d) are added. The amount of compound (b) added at the second step is such that the amount of the functional group in compound (b) is usually 5 to 65 moles, preferably 10 to 60 moles, per 100 moles of the isocyanate group.

An additional polymerization of polyfunctional isocyanate (a) with compound (b), compound (c) and compound (d) in the material composition of the present invention and a shaping of the polymerization mixture result in a shaped polymeric article.

The additional polymerization is carried out during, after or before the shaping. Preferably it is carried out during the shaping. The shaping is conducted usually by a melt shaping method, a casting shaping method, a dipping shaping method or a reaction extrusion shaping method. Of these, a reaction extrusion shaping method is preferable.

For the reaction extrusion shaping method, a procedure is employed wherein a molten material composition is extruded under heated conditions, while being, additionally polymerized, into a mold of a desired shape, followed by continuation of heating in the mold to complete the additional polymerization.

The additional polymerization is effected by heating the material composition. Preferably the heating is conducted after volatile ingredients such as a solvent and a dispersing medium, and air (contained as foams) are removed to an extent such that the total amount of these ingredients remaining in the material composition is usually not larger than 1% by weight, preferably not larger than 0.1% by weight. When the amount of such ingredients is larger than 1% by weight, the material composition is foamed upon heating and a shaped polymeric article having cells therein is produced.

When a reaction promotor is not used, the heating temperature is usually 60° to 170° C., preferably 100° to 130° C. At a temperature lower than 60° C., the additional polymerization is difficult to conduct. In contrast, at a temperature higher than 170° C., decomposition reactions occur and the shaped article is liable to be deteriorated. The heating time varies depending upon the particular shape of the shaped article, but is usually in the range of 6 to 120 hours, preferably 12 to 48 hours. When the heating time is short, the shaped article has a large permanent set. In contrast, when the heating time is long, the shaped article has a poor tensile strength. A reaction promotor can be added to promote the additional polymerization. As examples of the reaction promotor, there can be mentioned tertiary amines and organic tin compounds. By using the reaction promotor, the additional polymerization can be completed at a relatively low heating temperature and for a short period of time.

After completion of the additional polymerization, the polymerization product (i.e., shaped polymeric material) is usually allowed to stand for 4 to 14 days at room temperature to age the shaped article. By the aging, the permanent set of the shaped article is desirably reduced.

The shaped article of the present invention has a tensile strength at break of usually in the range of 15 to 50 MPa, preferably 18 to 40 MPa, an elongation at break of usually at least 550%, preferably at least 600% and more preferably at least 700%, and a permanent set (an elongation as measured after a tensile load is removed) of usually smaller than 20%, preferably not larger than 15%.

The invention will now be described specifically by the following examples, but should not be construed to be limited thereto.

The evaluation methods employed in the examples are as follows.

Tensile Test

A dumbbell specimen is punched out from a polymer sheet having a thickness of 2 mm by using a #3 dumbbell die as stipulated in Japanese Industrial Standard K6301, and gauge marks are drawn at an interval of 2 cm in the drawing direction on the surface of the specimen. The specimen is drawn at a grip distance of 20 mm and a grip separating rate of 400 mm/min under conditions of temperature of 23° C. and relative humidity of 65%, and the tensile strength and elongation at break are measured.

Permanent Set

A dumbbell specimen is punched out from a polymer sheet having a thickness of 2 mm by using a #3 dumbbell die as stipulated in Japanese Industrial Standard K6301, and gauge marks are drawn at an interval of 2 cm in the drawing direction on the surface of the specimen. The specimen is drawn at a grip distance of 20 mm and a grip separating rate of 400 mm/min under conditions of temperature of 23° C. and relative humidity of 65% until the specimen reaches an elongation of 500%. The specimen is maintained at the drawn state for 10 minutes. After the tensile load is removed, the specimen is allowed to stand for 10 minutes and the distance (m) between two gauge marks is measured. The permanent set is calculated as the ratio in % of the difference between the gauge mark distance (m) as measured after the tensile load is removed and the gauge mark distance as measured before drawing, (i.e., 2 cm) to the latter distance (2 cm).

Tear Test

A specimen having a rectangular shape with a length of 60 mm and a width of 12 mm, one long side of which has a notch, i.e., a V-shaped indentation having a depth of 2 mm at the center thereof (said indentation having a shape of triangle right-angled at the bottom of the V-shaped indentation), is punched out from a polymer sheet having a thickness of 2 mm. The specimen is drawn by the same procedure and under the same conditions as those employed for the tensile test, and the tear strength at break is measured.

Antithrombotic Property

A balloon catheter is inserted through the aorta to the vicinity of the right atrium of a goat, and physiologic saline is injected into the catheter to expand the balloon to a diameter of 1 cm. The catheter is allowed to stand for 10 minutes as the balloon is expanded, and then is deflated. Thirty minutes after the deflation, the catheter is withdrawn from the aorta, and the surface of the balloon is observed by the naked eye to check the occurrence of thrombus. The observation results are expressed by the following three ratings.

A: No thrombus occurred.

B: Thrombus occurred only to a slight extent such that the health of goat is not injured even though the catheter is repeatedly used.

C: Thrombus occurred to an extent such that repeated use of the catheter is apt to injure the health of goat.

Collective Evaluation as Material for Catheter Balloon

A material having a tensile strength of at least 15 MPa, an elongation of at least 550%, a permanent set of not larger than 20% and an antithrombosis of rating A is acceptable (expressed as "A"). Especially a material having a tensile strength of at least 20 MPa, an elongation of at least 600%, a permanent set of not larger than 15% and an antithrombosis of rating A is of excellent quality (expressed as "E"). A material not satisfying the above-mentioned acceptance criteria is unacceptable (expressed as "C").

Antikinking Property

A tube with a diameter of 2.3 mm for a catheter is placed at room temperature (20° C.) on two supporting blocks arranged at an interval of 40 mm , and a point of the tube positioned at equal distance from the two support blocks is pushed down at a rate of 5 mm/min. When kinking occurs, the distorted length of the pushed point (i.e., the depth of the V-shaped distorted tube) is measured.

Distortion Recovery

Both ends of a tube for a catheter having an axial length of 200 mm and a diameter of 23 mm are connected into a loop form by a self-adhesive tape, and the loopy tube is placed in a thermostatic chamber and maintained at 50° C. for 30 minutes. Then, the self-adhesive tape is removed and the tube is allowed to stand in a chamber maintained at a temperature of 20° C. for 10 minutes. Then the length (L in mm) of a segment of a straight line extending from one end of the tube to the other end thereof is measured. The distortion recovery (%) is calculated from the equation:

$$\text{Distortion recovery } (\%) = (L/200) \times 100$$

Collective Evaluation as Catheter Tube

A material having an antikinking degree of at least 25 mm and an ratio of distortion in length of at least 80% is acceptable and expressed as "A". A material not satisfying these acceptance criteria is expressed as "C"

Evaluation of Adhesion Retention

Two sheets of the same antithrombotic material are adhered to respective pumps of two auxiliary artificial hearts. One sheet is peeled at 37° C. and a peeling rate of 100 mm/min, and the strength (A) (kN/m) thereof is measured. The other sheet adhered to the pump is drawn to an elongation of 5% at 37° C. and this drawing is repeated 200,000 times. Thereafter, the sheet is peeled at 37° C. and a peeling rate of 100 mm/min, and the strength (B) (kN/m) thereof is measured. The adhesion retention is expressed by the ratio in % of the strength (B) as measured after the repeated drawing to the strength (A) as measured before the repeated drawing.

Example 1

A reactor flashed with nitrogen was charged with 100 milli-moles of diphenylmethane diisocyanate and 50 milli-moles of polyoxytetramethylene glycol having a number average molecular weight of 1,000 and a weight average molecular weight/number average molecular weight ratio of 1.86. The content was stirred at 90° C. for one hour to conduct an additional polymerization whereby a urethane prepolymer was obtained.

Into the reactor containing the urethane prepolymer, 25 milli-moles of polyoxytetramethylene glycol having a number average molecular weight of 1,000 and a weight average molecular weight/number average molecular weight ratio of 1.86, 22 millimoles of 1,4-butanediol and 2 millimoles of trimethylolpropane as chain extender were added at 70° C. The mixture was stirred and deaerated for 3 minutes by using a vacuum pump whereby a material composition was obtained.

The thus-obtained material composition was cast into a space (distance: 2 mm) between a pair of square iron sheets each having a size of 10 cm×10 cm, and heated at 110° C. for 24 hours to give a shaped article of a sheet-shape. The evaluation results of the sheet are shown in Table 1.

The above-mentioned urethane prepolymer and the above-mentioned chain extender were maintained at 70° C. and mixed together at that temperature by a mixer provided with a gear pump at a rate of 2 ml/min and at a pressure of 5 atm. The thus-obtained mixture (which is a material composition for medical use) was introduced into a column of an extruder having an inner volume of about 10 ml and maintained at a temperature of 130° to 170° C. where the mixture was subjected to an additional polymerization and extruded through a nozzle to form a coating around a core made of stainless steel wires with a diameter of 1.8 mm.

The coated stainless steel wire core was cooled by using a blower, traveled on a conveyor, and out by a cutter into a length of 5 to 12 cm. The cut product was heated at 110° C. for 24 hours and then immersed in an aqueous solution containing 70% of ethanol for 4 hours. Thereafter, the tublar coating was demolded from the stainless steel wire core, dried at 70° C. and then adjusted to a length of 1.5 cm.

The thus-prepared tube was fitted to a tip of an intravascular dwelling catheter so that the tube covers an opening for balloon on the wall of the tip portion of the tube to prepare a balloon catheter. The evaluation results of antithrombotic properly of the catheter balloon are shown in Table 1.

Examples 2 to 22 and Comparative Example 1 to 6

By the same procedures as described in Example 1, material compositions, sheets and balloon catheters were prepared wherein the compounds used and amounts thereof were varied as shown in Tables 1 through 5 with all other conditions remaining the same. The evaluation results of the sheets and balloon catheters are shown in Table 1 through Table 5.

TABLE 1

| | Examples | | | | |
|---|---|---|---|---|---|
| | 1 | 2 | 3 | 4 | 5 |
| Prepolymer | | | | | |
| Polyfunctional isocyanate (a) [m-mol] | | | | | |
| Diphenylmethane diisocyanate | 100 | 100 | 100 | 100 | 100 |
| Compound (b) [m-mol] | | | | | |
| Polyoxytetramethylene glycol | 50 | 50 | 50 | 50 | 50 |
| Number average molecular weight (Mn) | 1000 | 1500 | 1000 | 1000 | 2000 |
| Mw/Mn ratio *1 | 1.86 | 1.68 | 1.86 | 1.86 | 1.86 |
| Chain extender | | | | | |
| Compound (b) [m-mol] | | | | | |
| Polyoxytetramethylene glycol | 25 | 12 | 48 | 44 | 21 |
| Number average molecular weight (Mn) | 1000 | 1500 | 1000 | 1000 | 1000 |
| Mw/Mn ratio *1 | 1.86 | 1.68 | 1.86 | 1.86 | 1.86 |
| Compound (c) [m-mol] 1,4-Butanediol | 22 | 20 | 1.85 | 1 | 17 |
| Compound (d) [m-mol] Trimethylolpropane | 2 | 2 | 0.1 | 0.13 | 10 |
| Tensile strength [MPa] | 34 | 18 | 30 | 28 | 21 |
| Elongation [%] | 700 | 620 | 840 | 810 | 590 |
| Permanent set [%] | 4 | 10 | 18 | 17 | 13 |
| Tear strength [kN/m] | 50 | 28 | 40 | 35 | 40 |
| Antithrombotic property | A | A | A | A | A |
| Collective evaluation as balloon material | E | A | A | A | A |

*1 Mw/Mn ratio: Ratio of weight average molecular weight/number average molecular weight

TABLE 2

| | Examples | | | | |
|---|---|---|---|---|---|
| | 6 | 7 | 8 | 9 | 10 |
| Prepolymer | | | | | |
| Polyfunctional isocyanate (a) [m-mol] | | | | | |
| Methylenedicyclohexane-4,4'-diisocyanate | — | — | — | — | 100 |
| Diphenylmethane diisocyanate | 100 | 100 | 100 | 100 | — |
| Compound (b) [m-mol] | | | | | |
| Polyoxytetramethylene glycol | 50 | 50 | 50 | 50 | 50 |
| Number average molecular weight (Mn) | 1000 | 750 | 2000 | 1000 | 1000 |
| Mw/Mn ratio *1 | 1.85 | 1.85 | 1.81 | 1.86 | 1.86 |
| Chain extender | | | | | |
| Compound (b) [m-mol] | 13 | 43 | 13 | 23 | 23 |
| Polyoxytetramethylene glycol | | | | | |
| Number average molecular weight (Mn) | 1000 | 750 | 2000 | 1000 | 1000 |
| Mw/Mn ratio *1 | 1.86 | 1.85 | 1.81 | 1.86 | 1.86 |
| Compound (c) [m-mol] | | | | | |
| Ethylenediamine | — | — | — | — | 18 |
| 1,4-Butanediol | 26 | 1.3 | 18 | 1.3 | — |
| Compound (d) [m-mol] | | | | | |
| Glycerine | — | — | — | — | 1.3 |
| Trimethylolpropane | 6.7 | 0.13 | 2.7 | 0.13 | — |
| Tensile strength [MPa] | 33 | 22 | 25 | 20 | 28 |
| Elongation [%] | 570 | 620 | 700 | 610 | 560 |
| Permanent set [%] | 18 | 17 | 18 | 16 | 17 |
| Tear strength [kN/m] | 42 | 40 | 31 | 30 | 33 |
| Antithrombotic property | A | A | A | A | A |
| Collective evaluation as balloon material | A | A | A | A | A |

*1 Mw/Mn ratio: Ratio of weight average molecular weight/number average molecular weight

TABLE 3

| | Examples | | | | |
|---|---|---|---|---|---|
| | 11 | 12 | 13 | 14 | 15 |
| Prepolymer | | | | | |
| Polyfunctional isocyanate (a) [m-mol] | | | | | |
| Diphenylmethane diisocyanate | 100 | 100 | 100 | 100 | 100 |
| Compound (b) [m-mol] | | | | | |
| Polyoxytetramethylene glycol | 50 | 50 | 50 | — | — |
| Polypropylene oxide | — | — | — | 50 | — |

TABLE 3-continued

| | Examples | | | | |
|---|---|---|---|---|---|
| | 11 | 12 | 13 | 14 | 15 |
| Ethylene oxide/propylene oxide copolymer | — | — | — | — | 50 |
| Number average molecular weight (Mn) | 2700 | 650 | 1000 | 1000 | 1000 |
| Mw/Mn ratio *1 | 1.83 | 1.85 | 1.86 | 1.86 | 1.86 |
| Chain extender | | | | | |
| Compound (b) [m-mol] | | | | | |
| Polyoxytetramethylene glycol | 16 | 44 | 23 | — | — |
| Polypropylene oxide | — | — | — | 23 | — |
| Ethylene oxide/propylene oxide copolymer | — | — | — | 23 | — |
| Number average molecular weight (Mn) | 2700 | 650 | 1000 | 1000 | 1000 |
| Mw/Mn ratio *1 | 1.83 | 1.85 | 1.86 | 1.86 | 1.86 |
| Compound (c) [m-mol] | | | | | |
| 1,4-Butanediol | 32 | 3 | — | 18 | 18 |
| 1,4-Dimethylolbenzene | — | — | 18 | — | — |
| Compound (d) [m-mol] | | | | | |
| Trimethylolpropane | 1.3 | 1.3 | — | 1.3 | 1.3 |
| Ethylenediamine tetraethanol | — | — | 1.3 | — | — |
| Tensile strength [MPa] | 40 | 22 | 43 | 36 | 32 |
| Elongation [%] | 800 | 580 | 800 | 900 | 820 |
| Permanent set [%] | 17 | 7 | 16 | 18 | 16 |
| Tear strength [kN/m] | 31 | 29 | 39 | 37 | 31 |
| Antithrombotic property | A | A | A | A | A |
| Collective evaluation as balloon material | A | A | A | A | A |

*1 Mw/Mn ratio: Ratio of weight average molecular weight/number average molecular weight

TABLE 4

| | Examples | | | | | |
|---|---|---|---|---|---|---|
| | 16 | 17 | 18 | 19 | 20 | 21 |
| Prepolymer | | | | | | |
| Polyfunctional isocyanate (a) [m-mol] | | | | | | |
| Diphenylmethane diisocyanate | 100 | 100 | 100 | 100 | 100 | 100 |
| Compound (b) [m-mol] | | | | | | |
| Polyoxytetramethylene glycol | 50 | 50 | 45 | 55 | 50 | 50 |
| Number average molecular weight | 1100 | 1000 | 1000 | 1000 | 1000 | 1000 |
| Mw/Mn ratio *1 | 1.86 | 1.86 | 1.86 | 1.86 | 2.1 | 2.3 |
| Chain extender | | | | | | |
| Compound (b) [m-mol] | | | | | | |
| Polyoxytetramethylene glycol | 33 | 23 | 30 | 20 | 25 | 23 |
| Number average molecular weight (Mn) | 1100 | 1000 | 1000 | 1000 | 1000 | 1000 |
| Mw/Mn ratio *1 | 1.86 | 1.86 | 1.86 | 1.86 | 2.1 | 2.3 |
| Compound (c) [m-mol] | | | | | | |
| 1,4-Butanediol | 9.6 | 18 | 22 | 22 | 22 | 18 |
| Compound (d) [m-mol] | | | | | | |
| Trimethylolpropane | 0.26 | 1.3 | 2 | 2 | 2 | 1.3 |
| Tensile strength [MPa] | 16 | 37 | 27 | 28 | 15 | 19 |
| Elongation [%] | 820 | 840 | 710 | 620 | 570 | 610 |
| Permanent set [%] | 17 | 10 | 13 | 14 | 19 | 20 |
| Tear strength [kN/m] | 42 | 33 | 45 | 30 | 40 | 31 |
| Antithrombotic property | A | A | A | A | A | A |
| Collective evaluation as balloon material | A | E | E | E | A | A |

*1 Mw/Mn ratio: Ratio of weight average molecular weight/number average molecular weight

TABLE 5

| | Comparative Examples | | | | | |
|---|---|---|---|---|---|---|
| | 1 | 2 | 3 | 4 | 5 | 6 |
| Prepolymer | | | | | | |
| Polyfunctional isocyanate (a) [m-mol] | | | | | | |
| Diphenylmethane diisocyanate | 100 | 100 | 100 | 100 | 100 | 100 |
| Compound (b) [m-mol] | | | | | | |
| Polyoxytetramethylene glycol | 50 | 56 | 50 | 50 | 50 | 50 |
| Number average molecular weight (Mn) | 1000 | 1000 | 1000 | 400 | 4000 | 1000 |
| Mw/Mn ratio *1 | 1.86 | 1.86 | 1.86 | 2.4 | 2.2 | 1.86 |
| Chain extender | | | | | | |
| Compound (b) [m-mol] | | | | | | |
| Polyoxytetramethylene glycol | 7 | 53 | 8 | 25 | 25 | 28 |
| Number average molecular weight (Mn) | 1000 | 1000 | 1000 | 400 | 4000 | 1000 |
| Mw/Mn ratio *1 | 1.86 | 1.86 | 1.86 | 2.4 | 2.2 | 1.86 |
| Compound (c) [m-mol] | | | | | | |
| 1,4-Butanediol | 18 | 6 | 20 | 22 | 22 | 22 |
| Compound (d) [m-mol] | | | | | | |
| Trimethylolpropane | 1.3 | 2 | 14.7 | 2 | 2 | — |
| Tensile strength [MPa] | 13 | 18 | 13 | 25 | *2 | 18 |
| Elongation [%] | 480 | 990 | 320 | 400 | | 690 |
| Permanent set [%] | 2 | 24 | — | 8 | | 35 |
| Tear strength [kN/m] | 20 | 32 | 17 | 50 | | 32 |
| Antithrombotic property | A | A | — | B | | C |
| Collective evaluation as balloon material | C | C | C | C | C | C |

*1 Mw/Mn ratio: Ratio of weight average molecular weight/number average molecular weight
*2 Sheet could not be made As seen from the above data, when the amount of compound (b) is small (Comparative Example 1) or the amount of compound (d) is large (Comparative Example 3), the tensile strength and tear strength are reduced.

When the amount of compound (b) is large (Comparative Example 2), the permanent set becomes large. When the molecular weight of compound (b) is high (Comparative Example 5), the shaped article becomes difficult to make. In contrast, when the molecular weight of compound (b) is low (Comparative Example 4), the elongation is lowered and the antithrombotic property becomes poor.

When compound (d) is not used (Comparative Example 6) or the amount thereof is small, the permanent set is increased.

When compound (c) having two functional groups and compound (d) having three functional groups are incorporated in combination in the material composition, the shaped article made of a polymeric material prepared by an additional polymerization thereof exhibits enhanced tear strength and tensile strength and a reduced permanent set. When this shaped article is used as a balloon of a catheter, undesirable occurrence of thrombus can be avoided or minimized.

Especially when compound (d) having a narrow molecular weight distribution is used, the shaped polymeric article made from the material composition exhibits enhanced tensile strength and elongation and reduced permanent set, and, when this shaped article is used as a balloon of a catheter, undesirable occurrence of thrombus can be avoided or minimized.

Example 22, Comparative Example 7

By the same procedures as described in Example 1, a material composition was prepared wherein the kind of compounds and the amount thereof were varied as shown in Table 6 with all other conditions remaining the same.

The material composition was stirred at 70° C. by a mixer provided with a gear pump, and extruded under a pressure of 15 atm and at a rate of 2 ml/sec into a cylindrical column having an inner diameter of 20 mm, maintained at a temperature of 120° to 150° C., to give a 5 lumen tube having a diameter of 2.3 mm.

The tube was allowed to stand in a thermostatic chamber at 110° C. for 24 hours whereby the material composition was additionally polymerized to give a tube for catheter. The evaluation results of the tube are shown in Table 6.

TABLE 6

|  | Example 22 | Com. Ex. 7 |
|---|---|---|
| Prepolymer |  |  |
| Polyfunctional isocyanat (a) [m-mol] |  |  |
| Diphenylmethane diisocyanate | 100 | 100 |
| Compound (b) [m-mol] |  |  |
| Polyoxytetramethylens glycol | 50 | 50 |
| Number average molecular weight (Mn) | 1000 | 1000 |
| Mw/Mn ratio *1 | 1.86 | 2.2 |
| Chain extender |  |  |
| Compound (b) [m-mol] |  |  |
| Polyoxytetramethylene glycol | 15 | 15 |
| Number average molecular weight (Mn) | 1000 | 1000 |
| Mw/Mn ratio *1 | 1.86 | 2.2 |
| Compound (c) [m-mol] |  |  |
| 1,4-Butanediol | 32 | 34 |
| Compound (d) [m-mol] |  |  |
| Trimethylolpropane | 2 | — |
| Antikinking test [mm] | 30 | 17 |
| Distortion recovery [%] | 90 | 70 |
| Collective evaluation as tube material | A | C |

*1 Mw/Mn ratio: Ratio of weight average molecular weight/number average molecular weight As seen from Table 6, when a material composition comprising compound (b) and compound (c) but not comprising compound (d) is used (Comparative Example 7), the antikinking property and distortion resistance are not satisfactory. In contrast, the material composition of the present invention (Example 20) results in an additionally polymerized material giving a shaped article exhibiting a good antikinking property and distortion resistance.

Example 23

A reactor was flashed with nitrogen gas and was charged with 100 milli-moles of diphenylmenthane diisocyanate and charged 45 milli-moles of an etyhylene oxide-propylene oxide (ratio of 6/4 by mole) copolymer having a number average molecular weight of 1,000 and a weight average molecular weight/number average molecular weight ratio of 1.95. The content was maintained at 90° C. for 1 hour to conduct an additional polymerization. Then, 25 milli-moles of an ethylene oxide-propylene oxide (ratio of 6/4 by mole) copolymer having a number average molecular weight of 1,000 and a weight average molecular weight/number average molecular weight ratio of 1.86, 17 milli-moles of 1,4-butanediol, 3 milli-moles of trimethylolpropane and dioxane were incorporated into the reactor, and the mixture was maintained at 80° C. for 3 hours to conduct a reaction. Then ethanol was added to stop the reaction whereby a solution of a material composition was prepared.

The thus-prepared solution was coated on the inner wall of the pump of an auxilliary pump made of plasticized polyvinyl chloride. A sheet made of an antithrombotic polyurethane-silicone material was adhered onto the thus-formed coating to make an auxiliary artificial heart. The evaluation results thereof are shown in Table 7.

Comparative Example 8

By the same procedures as described in Example 23, a material composition was prepared and an auxiliary artificial heart was made therefrom wherein the compounds used and the amounts thereof were varied as shown in Table 7 with all other conditions remaining the same.

TABLE 7

|  | Example 23 | Com. Ex. 8 |
|---|---|---|
| Prepolymer |  |  |
| Polyfunctional isocyanate (a) [m-mol] |  |  |
| Diphenylmethane diisocyanate | 100 | 100 |
| Compound (b) [m-mol] |  |  |
| Ethylene oxide-propylene oxide copolymer | 45 | 45 |
| Number average molecular weight (Mn) | 1000 | 1000 |
| Mw/Mn ratio *1 | 1.66 | 2.2 |
| Chain extender |  |  |
| Compound (b) [m-mol] |  |  |
| Ethylene oxide-propylene oxide copolymer | 25 | 25 |
| Number average molecular weight (Mn) | 1000 | 1000 |
| Mw/Mn ratio *1 | 1.86 | 2.2 |
| Compound (c) [m-mol] |  |  |
| 1,4-Butanediol | 17 | 17 |
| Compound (d) [m-mol] |  |  |
| Trimethylolpropane | 3 | — |
| Adhesion Retention [%] | 88 | 74 |

*1 Mw/Mn ratio: Ratio of weight average molecular weight/number average molecular weight As seen from Table 7, the shaped polymeric article (polymer coating) made from the material composition of the present invention exhibits a good retention of adhesion.

Industrial Applicability

A shaped article composed of a polymeric material prepared by an additional polymerization of the material composition of the present invention exhibits a high tear strength, a high tensile strength, a large elongation, a reduced permanent set, a reduced toxicity and a good antithrombotic property.

Therefore, the above-mentioned shaped article is useful as catheters such as a tube catheter and a balloon catheter, an artificial heart, an artificial vessel and an artificial valve. The shaped article exhibits a high antithrombotic property even when it is used as parts for which a high stretchability is required, and therefore, it is especially useful as a balloon member of a medical balloon catheter.

We claim:

1. A shaped article of a tubular balloon form comprising a polymeric material prepared by an additional polymerization of:

(a) a polyfunctional isocyanate, (b) a compound having a molecular weight of 600 to 3,500 and two functional groups capable of being additionally polymerized with an isocyanate group, (c) a compound having a molecular weight not larger than 500 and two functional groups capable of being additionally polymerized with an isocyanate group; and (d) a compound having a molecular weight not larger than 700 and at least three functional groups capable of being additionally polymerized with an isocyanate group;

wherein the sum of the functional groups capable of being additionally polymerized with an isocyanate group, in compounds (c) and (d), is 1 to 35 moles per 100 moles of the isocyanate groups in polyfunctional isocyanate (a), the amount of the functional group capable of being additionally polymerized with an isocyanate group, in compound (d), is 0.1 to 18 moles per 100 moles of the isocyanate groups in polyfunctional isocyanate (a), the amount of the functional group capable of being additionally polymerized with an isocyanate group, in compound (b), is 60 to 100 moles per 100 moles of the isocyanate groups in polyfunctional isocyanate (a), and the sum of the functional groups capable of being additionally polymerized with an isocyanate group, in compounds (b), (c), and (d), is 80 to 110 moles per 100 moles of the isocyanate groups in polyfunctional isocyanate (a).

2. The shaped article according to claim 1, wherein the weight average molecular weight/number average molecular weight ratio of compound (b) is less than 2.

3. The shaped article according to claim 1, wherein the sum of the functional groups capable of being additionally polymerized with an isocyanate group, in compound (c) plus compound (d), is 3 to 35 moles per 100 moles of the isocyanate groups in polyfunctional isocyanate (a), the amount of the functional group capable of being additionally polymerized with an isocyanate group, in compound (d), is 1 to 10 moles per 100 moles of the isocyanate groups in polyfunctional isocyanate (a), the amount of the functional group capable of being additionally polymerized with an isocyanate group, in compound (b), is 70 to 95 moles per 100 moles of the isocyanate groups in polyfunctional isocyanate (a), and the sum of the functional groups capable of being additionally polymerized with an isocyanate group, in compounds (b), (c), and (d), is 85 to 105 moles per 100 moles of the isocyanate groups in polyfunctional isocyanate (a).

4. The shaped article according to claim 1, wherein the functional groups capable of being additionally polymerized with an isocyanate group, in compounds (b), (c), and (d), are hydroxyl groups or amino groups.

5. The shaped article according to claim 1, wherein polyfunctional isocyanate (a) is an aromatic diisocyanate, compound (b) is a polyether-diol, compound (c) is a diamine or a diol, and compound (d) is a triamine or a triol.

6. The shaped article according to claim 1, wherein polyfunctional isocyanate (a) is diphenylmethane diisocyanate, compound (b) is polyoxytetramethylene glycol, compound (c) is ethylene diamine or 1, 4-butanediol, and compound (d) is trimethylolpropane.

7. The shaped article according to claim 1, wherein the ratio of compound (c) to compound (d) is such that:

the amount of the functional group capable of being additionally polymerized with an isocyanate group, in compound (c), is 70 to 97% by mole based on the sum of the functional groups capable of being additionally polymerized with an isocyanate group, in compound (c) plus compound (d), and the amount of the functional group capable of being additionally polymerized with an isocyanate group, in compound (d), is 3 to 30% by mole based on the sum of the functional groups capable of being additionally polymerized with an isocyanate group, in compound (c) plus compound (d).

8. The shaped article according to claim 1, wherein the shaped article has a tensile strength of 15 to 50 MPa, an elongation of at least 550% and a permanent set of not larger than 20%.

9. The shaped article according to claim 1, which has a tensile strength of 18 to 40 MPa, an elongation of at least 600%, and a permanent set of not larger than 15%.

10. A process for making a shaped article of a tubular balloon form comprising a polymeric material prepared by an additional polymerization of:

(a) a polyfunctional isocyanate, (b) a compound having a molecular weight of 600 to 3,500 and two functional groups capable of being additionally polymerized with an isocyanate group, and (c) a compound having a molecular weight not larger than 500 and two functional groups capable of being additionally polymerized with an isocyanate group, and (d) a compound having a molecular weight not larger than 700 and at least three functional groups capable of being additionally polymerized with an isocyanate group;

wherein the sum of the functional groups capable of being additionally polymerized with an isocyanate group, in compounds (c) and (d), is 1 to 35 moles per 100 moles of the isocyanate groups in polyfunctional isocyanate (a).

the amount of the functional group capable of being additionally polymerized with an isocyanate group, in compound (d), is 0.1 to 18 moles per 100 moles of the isocyanate groups in polyfunctional isocyanate (a).

the amount of the functional group capable of being additionally polymerized with an isocyanate group, in compound (b), is 60 to 100 moles per 100 moles of the isocyanate group in polyfunctional isocyanate (a), and the sum of the functional groups capable of being additionally polymerized with an isocyanate group, in compounds (b), (c), and (d), is 80 to 110 moles per 100 moles of the isocyanate groups in polyfunctional isocyanate (a);

said process comprising mixing polyfunctional isocyanate (a) and part of compound (b) together to form a mixture; heating the mixture; adding the remainder of compound (b), compound (c), and compound (d) to the heated mixture, while being stirred; shaping the resulting mixture into a tubular form, and then, heating the tubular form at a temperature of 60° to 170° C.

11. The process for making a shaped article of a tubular balloon form according to claim 10, wherein said shaping of the mixture into a tubular form is carried out by a reaction extrusion shaping method.

12. A balloon catheter comprising a catheter tube having a shaped article of a tubular balloon fitted to a tip portion of said catheter tube;

said shaped article of a tubular balloon form being made of a polymeric material prepared by an additional polymerization of:

(a) a polyfunctional isocyanate, (b) a compound having a molecular weight of 600 to 3,500 and two functional groups capable of being additionally polymerized with an isocyanate group, and (c) a compound having a molecular weight not larger than 500 and two functional groups capable of being additionally polymerized with an isocyanate group, and (d) a compound having a molecular weight not larger than 700 and at least three functional groups capable of being additionally polymerized with an isocyanate group;

wherein the sum of the functional groups capable of being additionally polymerized with an isocyanate group, in compounds (c) and (d), is 1 to 35 moles per 100 moles of the isocyanate groups in polyfunctional isocyanate (a), the amount of the functional group capable of being additionally polymerized with an isocyanate group, in compound (d), is 0.1 to 18 moles per 100 moles of the isocyanate groups in polyfunctional isocyanate (a), the amount of the functional group capable of being additionally polymerized with an isocyanate group, in compound (b), is 60 to 100 moles per 100 moles of the isocyanate groups in polyfunctional isocyanate (a), and the sum of the functional groups capable of being additionally polymerized with an isocyanate group, in compounds (b), (c), and (d), is 80 to 110 moles per 100 moles of the isocyanate groups in polyfunctional isocyanate (a).

13. The balloon catheter according to claim 12, wherein the weight average molecular weight/number average molecular weight ratio of compound (b) is less than 2.

14. The balloon catheter according to claim 12, wherein the sum of the functional groups capable of being additionally polymerized with an isocyanate group, in compound (c) plus compound (d), is 3 to 35 moles per 100 moles of the isocyanate groups in polyfunctional isocyanate (a), the amount of the functional group capable of being additionally polymerized with an isocyanate group, in compound (d), is 1 to 10 moles per 100 moles of the isocyanate groups in polyfunctional isocyanate (a), the amount of the functional group capable of being additionally polymerized with an isocyanate group, in compound (b), is 70 to 95 moles per 100 moles of the isocyanate groups in polyfunctional isocyanate (a), and the sum of the functional groups capable of being additionally polymerized with an isocyanate group, in compounds (b), (c), and (d), is 85 to 105 moles per 100 moles of the isocyanate groups in polyfunctional isocyanate (a).

15. The balloon catheter according to claim 12, wherein the functional groups capable of being additionally polymerized with an isocyanate group, in compounds (b), (c), and (d), are hydroxyl groups or amino groups.

16. The balloon catheter according to claim 12, wherein polyfunctional isocyanate (a) is an aromatic diisocyanate, compound (b) is a polyether-diol, compound (c) is a diamine or a diol, and compound (d) is a triamine or a triol.

17. The balloon catheter according to claim 12, wherein polyfunctional isocyanate (a) is diphenylmethane diisocyanate, compound (b) is polyoxytetramethylene glycol, compound (c) is ethylene diamine or 1,4-butanediol, and compound (d) is trimethylolpropane.

18. The balloon catheter according to claim 12, wherein the ratio of compound (c) to compound (d) is such that:

the amount of the functional group capable of being additionally polymerized with an isocyanate group, in compound (c), is 70 to 97% by moles based on the sum of the functional groups capable of being additionally polymerized with an isocyanate group, in compound (c) plus compound (d), and the amount of the functional group capable of being additionally polymerized with an isocyanate group, in compound (d) is 3 to 30% by mole based on the sum of the functional groups capable of being additionally polymerized with an isocyanate group, in compound (c) plus compound (d).

19. The balloon catheter according to claim 12, wherein the shaped article has a tensile strength of 15 to 50 MPa, an elongation of at least 550% and a permanent set of not larger than 20%.

20. The balloon catheter according to claim 12, wherein the shaped article has a tensile strength of 18 to 40 MPa, an elongation of at least 600% and a permanent set of not larger than 15%.

* * * * *